United States Patent [19]
Dubrul

[11] Patent Number: 5,454,790
[45] Date of Patent: Oct. 3, 1995

[54] METHOD AND APPARATUS FOR CATHETERIZATION ACCESS

[75] Inventor: William R. Dubrul, Redwood City, Calif.

[73] Assignee: Innerdyne, Inc., Sunnyvale, Calif.

[21] Appl. No.: 240,059

[22] Filed: May 9, 1994

[51] Int. Cl.$^6$ .................................................. A61M 29/00
[52] U.S. Cl. .......................... 604/104; 604/105; 604/164; 604/178
[58] Field of Search ...................... 604/104, 105, 604/284, 103, 106, 107, 264, 178, 175, 163, 164

[56] References Cited

U.S. PATENT DOCUMENTS

| | | | |
|---|---|---|---|
| 2,616,429 | 11/1952 | Merenlender | 604/105 |
| 3,490,457 | 1/1970 | Petersen | 604/105 |
| 3,948,271 | 4/1976 | Akiyama | 128/350 |
| 4,077,412 | 3/1978 | Moossun | 128/347 |
| 4,112,932 | 9/1978 | Chiulli | 128/3 |
| 4,141,364 | 2/1979 | Schultze | 128/349 |
| 4,589,868 | 5/1986 | Dretler | 604/96 |
| 4,871,358 | 10/1989 | Gold | 604/271 |
| 5,074,867 | 12/1991 | Wilk | 606/128 |
| 5,102,401 | 4/1992 | Lambert et al. | 604/264 |
| 5,176,649 | 1/1993 | Wakabayashi | 604/164 |
| 5,183,464 | 2/1993 | Dubrul et al. | 128/3 |
| 5,183,471 | 2/1993 | Wilk | 604/284 |
| 5,248,302 | 9/1993 | Patrick et al. | 604/178 |
| 5,344,439 | 9/1994 | Otten | 604/105 X |

FOREIGN PATENT DOCUMENTS 03585920   5/1990   European Pat. Off. .

OTHER PUBLICATIONS

Cope, C. "New Foley Catheter Introducer for Percutaneous Nephrostomy" *Urology* 27(6):606, Jun. 1981.

Weigele, J. B., et al. "Expandable Intravascular Catheter: Percutaneous Use for Endoluminal Retrievals" *Radiology* Nov., 1992, pp. 604–606.

Vorwerk, D., et al. "Percutaneous Embolectomy: In Vitro Investigations of the Self–expanding Tulip Sheath" *Radiology* 1992 182(2):415–418.

*Primary Examiner*—John D. Yasko
*Attorney, Agent, or Firm*—Townsend and Townsend and Crew

[57] ABSTRACT

An apparatus and method for percutaneous placement of access tubes, such as feeding and drainage tubes, vascular catheters, and the like, comprises an elastic access tube in an internal stylet. The stylet is received within a central lumen of the access tube and is used to axially elongate the tube, resulting in a reduced diameter. In a first embodiment, the diameter of the access tube is reduced sufficiently so that it can be placed through a relatively narrow penetration and so that it will radially expand by an amount sufficient to cause a tight anchor and seal against the penetration when the stylet is removed. In a second embodiment, the stylet has a sharpened distal tip which extends beyond the distal end of the access tube when in its axially extended configuration. The sharpened tip allows self-introduction of the assembly of access tube and stylet. In a third embodiment, a distal portion of the access tube is covered with a lubricous sheath. The lubricous sheath facilitates use of the assembly in combination with a dilation member which is radially expanded when the assembly of access tube and stylet is introduced therethrough.

69 Claims, 9 Drawing Sheets

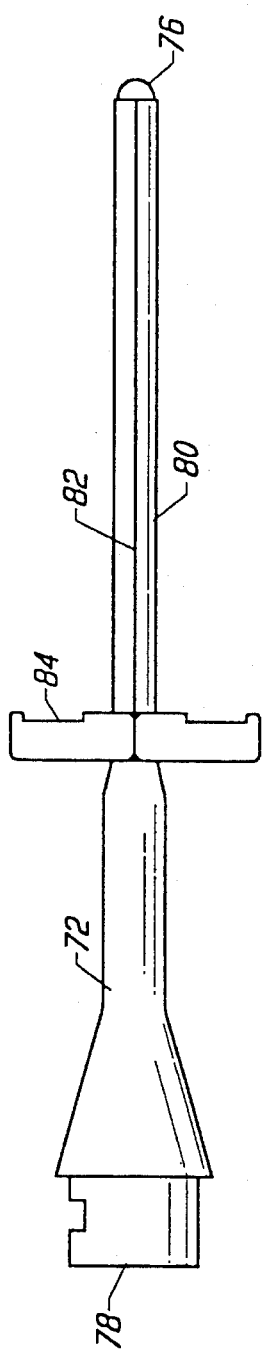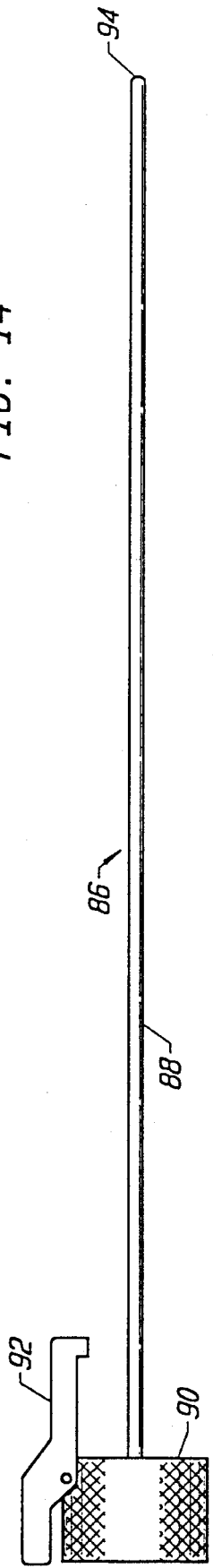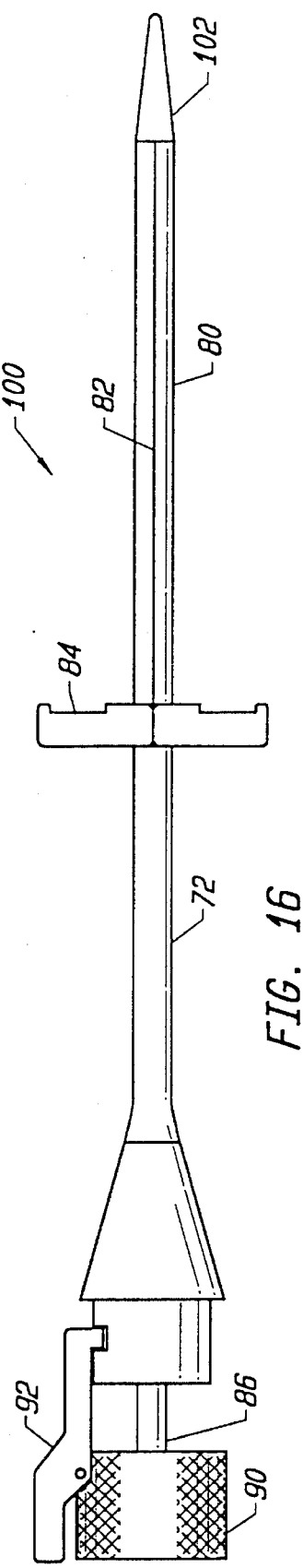

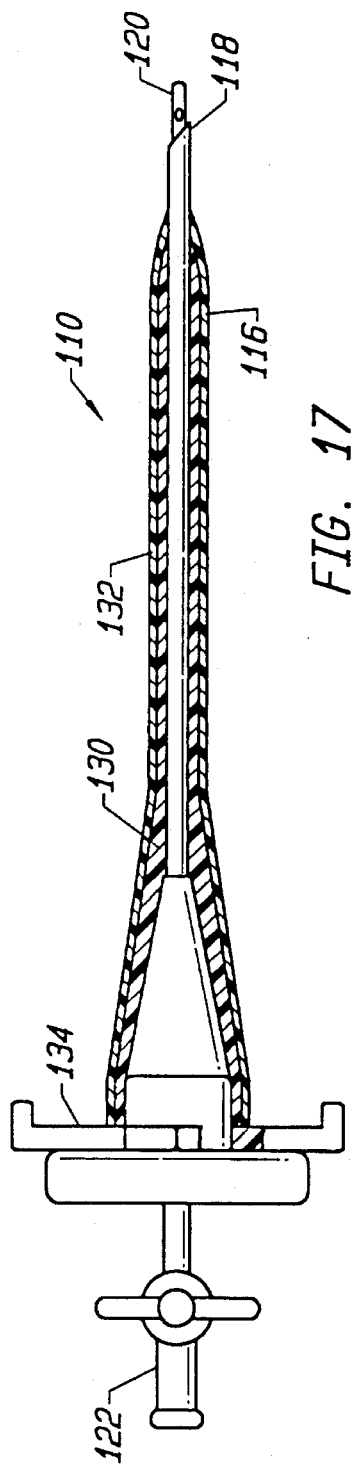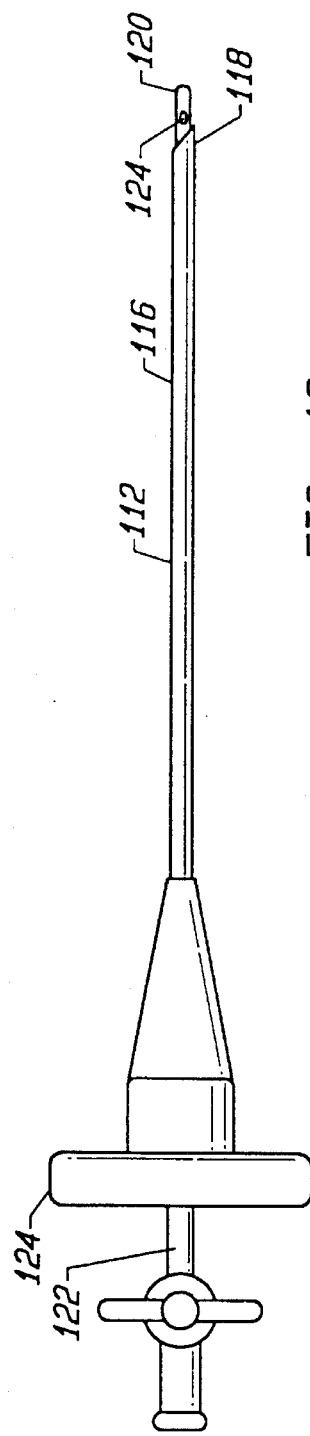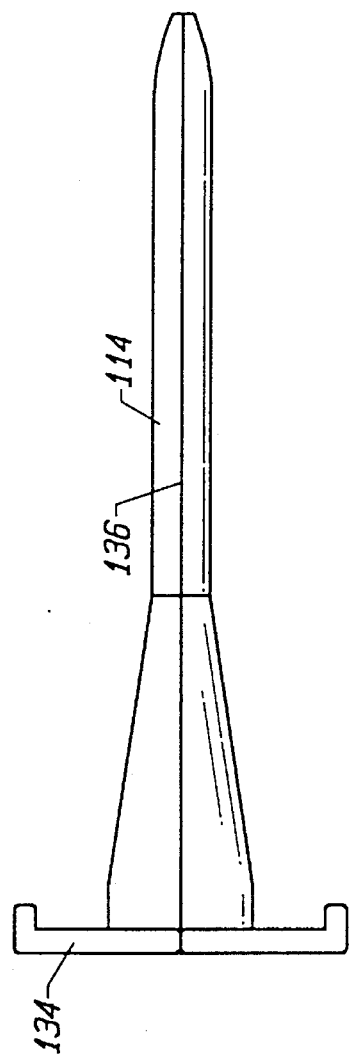

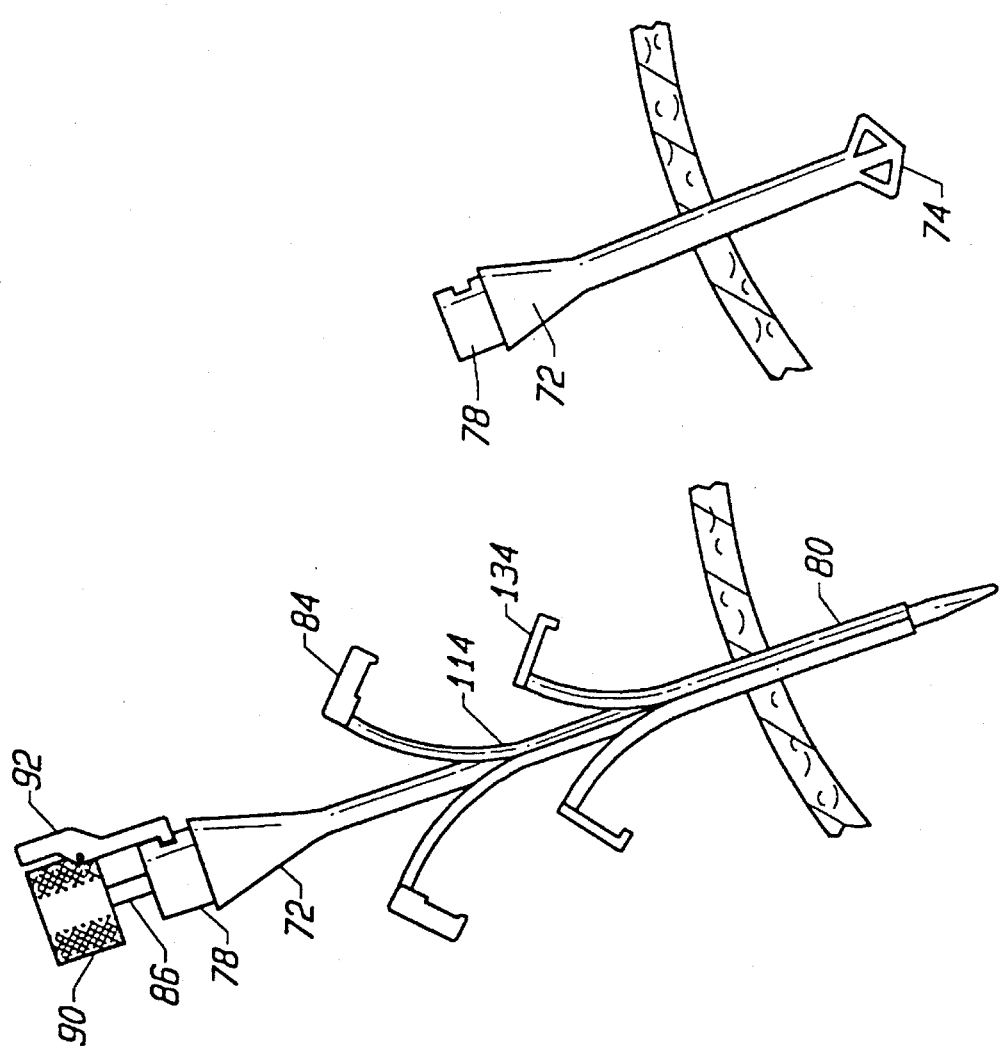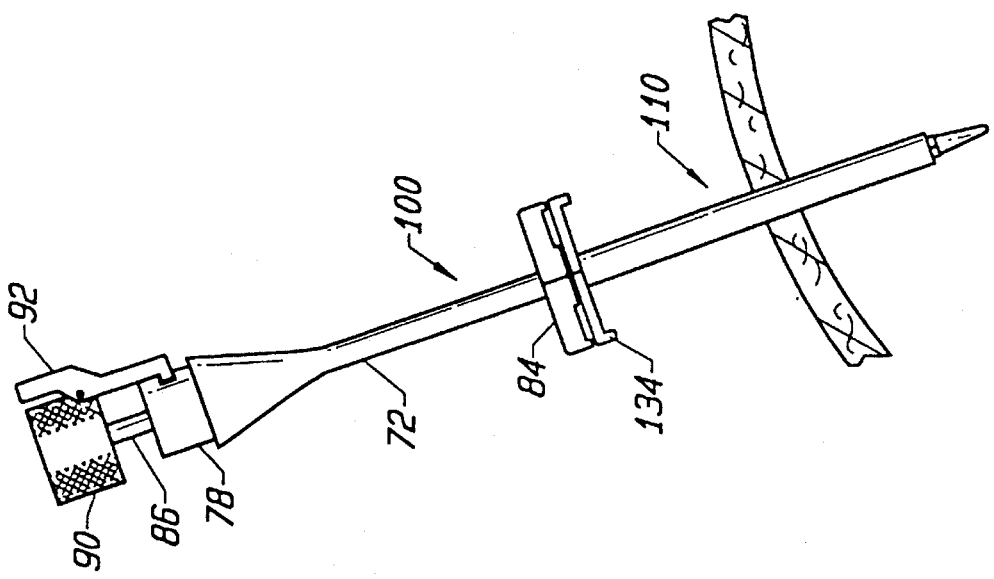

METHOD AND APPARATUS FOR CATHETERIZATION ACCESS

BACKGROUND OF THE INVENTION

1. Field of the Invention

The present invention relates generally to apparatus and methods for providing percutaneous access to internal body cavities and lumens for drainage, feeding, and other purposes. More particularly, the present invention relates to apparatus and methods for placing an elastic access tube within a percutaneous penetration to a target location within a patient's body.

Numerous catheterization procedures rely on initial formation of a percutaneous penetration through a patient's skin and subsequent insertion of a tubular catheter through the penetration into a body cavity or other target location. Catheterization is performed for a wide variety of purposes, including vascular access for performing diagnostic, interventional, and therapeutic procedures; drainage; feeding, and the like.

Of particular interest to the present invention, flexible catheters are frequently introduced to the kidneys, bladder, chest, lungs, gallbladder, and peritoneum, for drainage, and to the stomach, jejunum, duodenum, and large and small intestines for feeding. Such drainage and feeding catheters can be left in place for prolonged periods, frequently weeks or months, and may require periodic exchange as the catheters become blocked, dislodged, or otherwise ineffective.

Drainage and feeding procedures are frequently performed with a relatively simple elastomeric catheter referred to as a Foley catheter. The Foley catheter is an elastomeric tube having an inflatable balloon anchor near its distal end. The Foley catheter is typically introduced through a previously formed penetration so that the balloon lies within the body cavity of interest. The balloon is then inflated as an anchor, and drainage or feeding effected through a lumen of the catheter body. Foley catheters are widely used in percutaneous nephrostomies, bladder drainage procedures, jejunostomies, gastrostomies, and the like. In place of such expandable balloon structures, other conventional drainage and feeding catheters employ expandable Malecot structure at their distal ends.

For long-term placement, it is necessary that both feeding and drainage catheters be firmly anchored in place and sealed within the percutaneous penetration in order to lessen the risk of leakage, infection, and the like. It is also necessary, however, that the catheters be readily removable so that the catheters can be replaced when fouling occurs or for other reasons.

The ability to balance the requirements for firm anchoring and sealing within the percutaneous penetration with ease of replaceability has been particularly difficult in the case of feeding catheters used in gastrostomy procedures. The most common technique for placing feeding tubes is referred to as "percutaneous endoscopic gastrostomy," where an endoscope is introduced through the throat and into the stomach to locate a desired insertional location. Once the location is identified, a light on the endoscope allows the physician to use a needle to introduce a guidewire into the stomach. The guidewire is snared with a device introduced through the endoscope, and the guidewire is pulled out through the mouth. The guidewire is then used to pull a long, tapered gastrostomy tube inward through the mouth, to the stomach, and outward through the penetration. The taper provides an effective seal within the percutaneous penetration, and a permanently expanded "mushroom" on the tube prevents accidental withdrawal of the tube. While effective in many ways, such percutaneous endoscopic gastrostomy procedures suffer from certain disadvantages. The procedures can cause infections as the device must be drawn through the mouth and esophagus (where bacteria are prevalent) and into the freshly created wound site. The procedures require that the endoscope be introduced through the esophogus twice. Often, the second placement is very difficult because of damage caused during the first placement. More importantly, the permanently anchored feeding tube which is placed through such procedures is very difficult to remove and must be withdrawn through the patient's mouth, requiring yet another placement of the endoscope.

Improvements on the Foley catheter have been proposed by Dr. Constantin Cope, where a Foley catheter may be stiffened and thinned prior to introducing through a previously formed tissue penetration. Stiffening is achieved using an internal introducer rod which engages a distal end of the catheter and elongates the tube by a small amount. Such improved Foley catheters have been proposed for use in nephrostomy and urinary diversion procedures. While such improved Foley catheters are easier to introduce through previously formed tissue penetrations, they do not generally result in dilation of the tissue tract (thus limiting their ability to provide an enlarged access lumen) and they cannot be introduced in a single step procedure.

For these reasons, it would be desirable to provide improved access tubes, systems, and methods useful in a wide variety of patient catheterization procedures, including gastrostomy, nephrostomy, jejunostomy, urinary diversion, and the like. Such tubes, systems, and methods should allow for easy placement and removal of the access tube, while at the same time resulting in firm anchoring and sealing of the access tube within a percutaneous penetration. It would also be desirable to provide access tubes which are capable of direct introduction, i.e., are self-introducing, or which would be capable of introduction in combination with separate dilation or other percutaneous introduction procedures. Preferably, the access tubes will be self-sealing and/or self-anchoring within the percutaneous penetration, preferably being radially expandable within the penetrations to provide self-anchoring and relatively large access lumens.

2. Description of the Background Art

Use of an internal rod for elongating and stiffening a Foley catheter for introduction through a fresh or established nephrostomy tract is described in Cope (1981) Urology 27:606. See also, Cope et al. *Atlas of Interventional Radiology*, Lippencott, 1990, pages 11.5–11.6. Percutaneous embolectomy using a sheath having a self-expanding distal end which is maintained in a reduced diameter configuration by applying axial tension with an internal stylet is described in Vorwerk et al. (1992) Radiology 187:415–418; Weigele et al. (1992) Radiology (1992) 185:604–606; and European Patent Application 385 920. A drain for the eardrum which is inserted using a sharpened internal stylet is described in U.S. Pat. No. 3,948,271. U.S. Pat. No. 5,102,401, describes a catheter formed from a hydrophilic material which expands when exposed to a wet environment. A radially expanding dilator is described in U.S. Pat. No. 5,183,464. A radially expanding endotracheal tube is described in U.S. Pat. No. 4,141,364. Other percutaneously introduced tubes and sheaths are described in U.S. Pat. Nos. 5,183,471; 5,176,649; 5,074,867; 4,871,358; 4,589,868; 4,112,932; and 4,077,412.

SUMMARY OF THE INVENTION

According to the present invention, improved apparatus and methods for introducing and anchoring an access tube through a tissue penetration in a patient body are provided. The access tube can be used for a variety of conventional purposes, such as drainage, feeding, and the like, and comprises an elastic tubular body having a proximal end, a distal end, and a central lumen extending from the proximal end to the distal end. The tubular body has an intrinsic length and intrinsic outer diameter when not under axial tension or radial compression. A stylet is received within the central lumen and couples to the distal end of the access tube. The stylet is longer than the intrinsic length so that the access tube can be elongated and narrowed by advancing the stylet to place the tube under tension. Typically, the stylet will have a latch mechanism for releasably securing the proximal end of the access tube, wherein the latch mechanism is located at a distance from a distal end of the stylet which is at least 20% longer than the intrinsic length of the access tube. In this way, the diameter of the access tube can be reduced by at least 10%. An exemplary access tube has a length in the range from about 10 cm to 20 cm and an intrinsic outer diameter in the range from 5 mm to 8 mm, and the latch mechanism is located at a distance from the distal end of the stylet in the range from 15 cm to 40 cm.

In a preferred aspect, the access tube assembly will include a removable sheath covering at least a distal portion of the access tube and having an inner diameter which is less than the intrinsic outer diameter of the access tube. The sheath will thus be able to maintain a reduced diameter over the distal portion of the access tube and will reduce friction of the assembly as it is introduced through tissue or through a separate dilator, as will be described hereinafter. In a further preferred aspect, the access tube will have an expandable anchor near its distal end, usually in the form of a malecot structure or an inflatable balloon. The removable sheath will typically have a diameter in the range from 4 mm to 7 mm and will be axially scored or split along one side to facilitate removal, as also described hereinafter.

The access tube assembly of the present invention may further comprise an elongate dilation member including a radially expandable tubular body having a proximal end, a distal end, and an axial lumen therethrough. The dilation member will typically include a penetration member at its distal end so that it may be self-introduced through the patient's skin to a target location. The access tube may then be introduced through the dilation member, where the access tube usually acts to radially expand the dilation member as the access tube is being introduced. Typically, the dilation member will then be removed, and tension will then be released on the access tube to permit it to expand and anchor within the tissue penetration.

In another aspect and embodiment of the present invention, an access tube assembly comprises an elastic access tube and stylet, generally as described above. The stylet, however, will include a penetration element at or near its distal end, where the penetration element extends distally beyond the access tube when the stylet is in place in the central lumen of the access tube. The access tube will be removably coupled to the stylet on a proximal side of the penetration element. Axial tension will be placed on the access tube in order to reduce its diameter. The resulting assembly can be directly introduced through the patient's skin, and the stylet removed after introduction in order to release tension on the access tube and allow the tube to expand and anchor within the penetration.

According to the method of the present invention, a penetration is formed through tissue to a target location, either simultaneously with or prior to introducing an access tube. The access tube is under sufficient axial tension so that the outer diameter of the tube is at least 10% less than the intrinsic diameter of the tube when it is not under axial tension. Once in place within the tissue penetration, axial tension is released so that the diameter of the tube expands to dilate and seal against peripheral tissue of the penetration. The target location will typically be a hollow body organ, such as the stomach, intestines, kidney, gallbladder, chest, lungs, bladder, and the like; a blood vessel; or a disease artifact, such as a cyst.

The access tube assembly may itself be used to form the tissue penetration, e.g., when a penetration element is provided at its distal tip. Alternatively, the tensioned access tube may be introduced through a previously formed penetration, e.g., a penetration formed using a conventional stylet or other penetrating member. Additionally, the access tube may be introduced in conjunction with a dilation procedure where a narrow diameter penetration is first formed and is thereafter radially expanded in order to increase the size of access tube which may be placed. Such dilation may occur prior to introducing the access tube of the present invention, or alternatively the access tube may be used as an element in a dilation system which results with placement of the access tube in a radially dilated tissue penetration.

Each of these aspects of the present invention will be better understood when considered in conjunction with the following description of the specific embodiments.

BRIEF DESCRIPTION OF THE DRAWINGS

FIGS. 14–19 illustrate the components of a third access tube assembly including a self-introducing dilation member constructed in accordance with the principles of the present invention.

FIGS. 20–24 illustrate the method of use of the access tube assembly of FIGS. 14–19 and forming a tissue penetration and placing an access tube through the tissue penetration.

DESCRIPTION OF THE SPECIFIC EMBODIMENT

Figure 1:
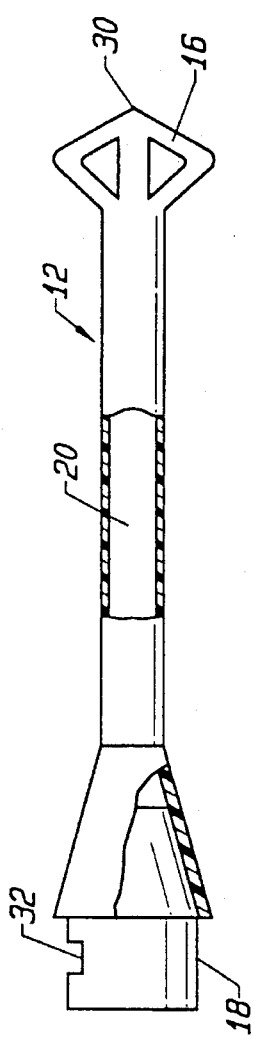
FIGS. 1–3 illustrate the components of a first access tube assembly constructed in accordance with the principles of the present invention.

Apparatus and methods of the present invention are used to percutaneously place an elastic access tube in a patient to provide access to a target location, typically a hollow body organ or cavity or another region to be treated, such as a cyst. The access tube will typically be used for draining target locations, such as the bladder, kidney, chest, lungs, gallbladder, peritoneum, intestines, cysts and the like. The access tube will also find use for feeding patients by insertion into the stomach. By "percutaneous" it is meant that the access tube will be placed through the patient's outer skin and, optionally, through intermediate tissue and organ structures to reach the desired body cavity or other location. Particular apparatus and methods for percutaneously introducing the access tubes will be described in more detail hereinafter. In some cases, the access tube could also be used to provide peripherally sealed access to the vascular system.

The access tube comprises an elastic tubular body having an intrinsic length in the range from 2 cm to 20 cm, usually being from 10 cm to 20 cm for drainage and feeding catheters and an intrinsic diameter in the range from 2 mm to 8 mm, usually being from 5 mm to 8 mm for drainage and feeding catheters. The tubular body may be composed of any medically acceptable elastic material, such as latex, silicone rubber, and the like. The "intrinsic" length and diameter are the length and diameter of the tube while not under axial stress or radially compression. The length may be increased, and the diameter reduced, by placing the tubular body under axial tension, typically using a stylet as described hereinafter. The tubular body will be "stretchable" by at least about 20%, usually at least about 30%, and preferably at least about 50%. The corresponding reduction in diameter will be at least about 10%, usually at least about 15%, often at least about 20%, and preferably at least about 25%.

The above dimensions are appropriate for drainage and feeding catheters. For vascular access, the dimensions will generally be smaller. The intrinsic length will generally be from 2 cm to 10 cm and the intrinsic diameter will generally be from 2 mm to 5 mm.

The access tube will usually have an expandable anchor at or near its distal end, typically in the form of a Malecot, an inflatable balloon (in the nature of a Foley catheter), a pigtail (in the nature Cope loop catheter), and the like. The access tube will usually also have a proximal fitting, both for connecting a drain tube, feeding tube, or the like, to the access tube, and for latching the proximal end of the access tube to the stylet to maintain axial tension and elongation.

For drainage access, a suction reservoir or drainage bag may be attached via a drain tube which is secured to the proximal fitting. For feeding access, a nutrient solution may be provided via a feeding tube which is secured to the proximal fitting. For vascular access, the fitting will usually include a hemostatic valve to permit introduction of a vascular catheter and associated guiding catheters, guide wires, and the like. Vascular catheters are available for both diagnostic procedures, such as angiography and ultrasonic imaging, and interventional procedures, such as angioplasty, atherectomy, laser ablation, stent placement, graft placement, and the like.

The stylet will be a simple rod structure having a length greater than that of the tubular body of the access tube. Typically, the length of the stylet will be from 15 cm to 45 cm, usually from 20 cm to 40 cm, and preferably from 20 cm to 30 cm. The distal end of the stylet will be adapted to engage or couple to the distal end of the access tube in order to permit axial translation of the stylet to apply the desired tension to the access tube. In the simplest case, the distal end of the stylet may be a blunt tip, where the blunt tip engages a closed end of the access tube. In other cases, the stylet may have a collar or other fitting for engaging the distal end of the access tube, particularly when the stylet has a sharpened tip which extends distally beyond the distel end of the access tube. Such a sharpened tip is useful to permit self-introduction of the combination of access tube and stylet, as described in more detail hereinafter.

The assembly of access tube and stylet may further include an elongate dilation member which includes a penetration element for self-introduction. The dilation member may be similar to the radially expanding dilator described in application Ser. No. 08/026,922, the full disclosure which is incorporated herein by reference. Briefly, the dilation member will be a tubular body having a distal end, a proximal end, and an axial lumen therebetween. The tubular body will be radially expandable so that the combination of access tube and stylet may be advanced therethrough after the dilation member has been percutaneously introduced. In the exemplary embodiment herein, the dilation member includes an elastic tubular member covered by a lubricous sheath. The dilation member is introduced using an internal needle which is removed prior to introducing the access tube and sheath. Other radially expansible dilating members would also find use in the present invention.

Figure 2:
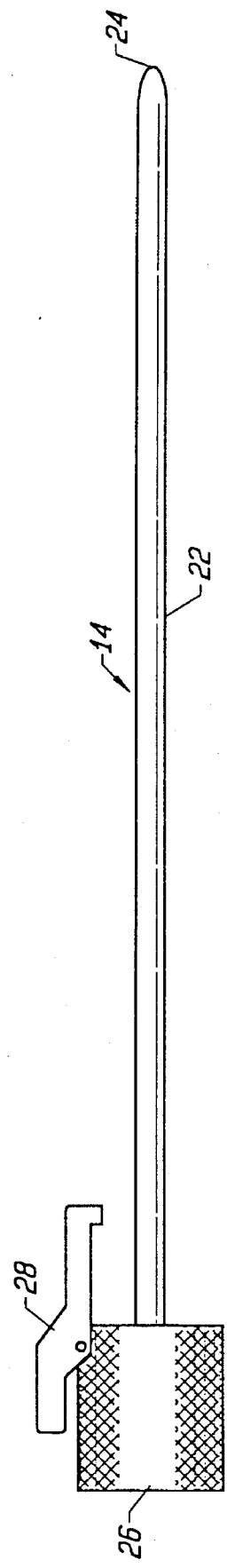
Figure 3:
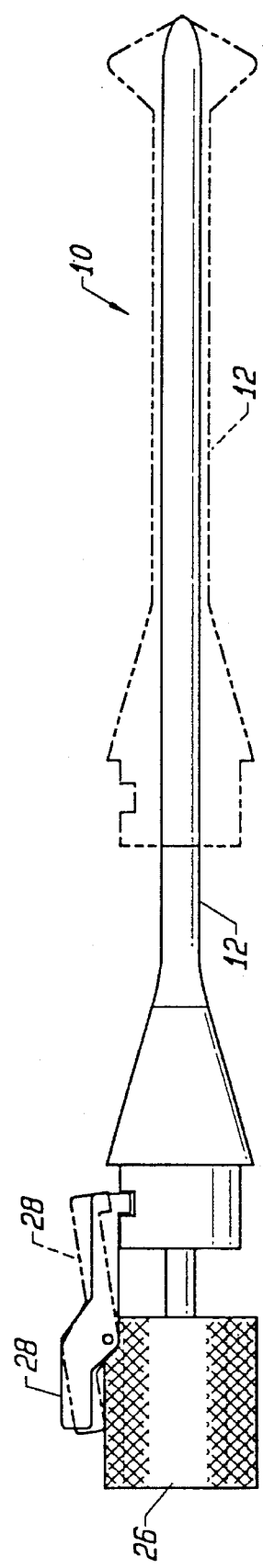

Referring now to FIGS. 1–3, a first access tube assembly 10 (FIG. 3) comprises an access tube 12 (FIG. 1) and a stylet 14 (FIG. 2). The access tube 12 is shown in its relaxed configuration in FIG. 1 and its axially extended configuration in FIG. 3. For comparison, the profile of the relaxed configuration of the access tube 12 is illustrated in broken line in FIG. 3. The access tube 12 includes a Malecot structure 16 at its distal end and a fitting 18 at its proximal end. The fitting 18 defines a port (not illustrated) which communicates with a central lumen 20 extending the full length of access tube 12. The stylet 14 includes an elongate rod 22 having a blunt tip 24 at its distal end. A finger grip 26 is secured to the proximal end of the rod 22 and includes a latch member 28. When inserted fully into the access tube 20, the stylet 14 engages a closed distal tip 30 of the Malecot structure 16 and axially stretches the tubular body of the access tube, as illustrated in FIG. 3. The latch member 28 engages a recess 32 formed on the proximal fitting 18. In this way, the access tube 12 can be stretched in order to reduce its diameter, as described above, and maintained in the stretched configuration by the latch member 28. The latch mechanism 28 will be located from 3 cm to 40 from the distal end of the stylet, preferably being from 15 cm to 40 for feeding and drainage uses and from 3 cm to 20 cm for vascular access. When desired, the access tube 12 may be released by depressing the latch member 28, as illustrated in broken line in FIG. 3. The access tube is then free to shorten and radially expand as a result of its elastic nature.

Figure 6:
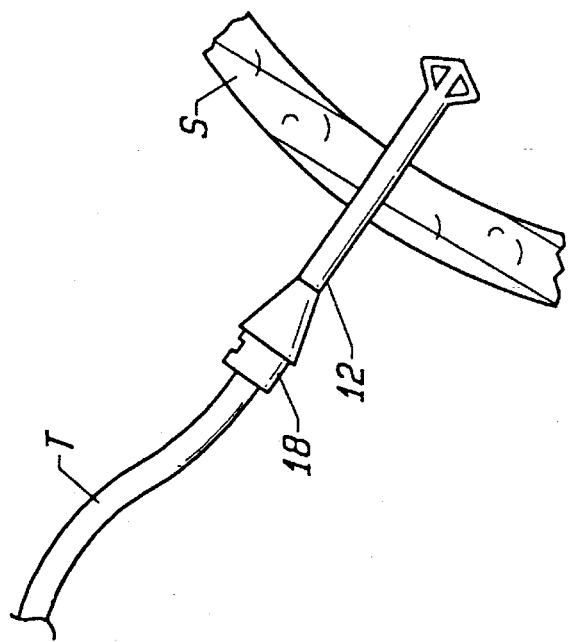
FIGS. 4–6 illustrate use of the access tube assembly of FIGS. 1–3 in placing an access tube through a tissue penetration.
Figure 5:
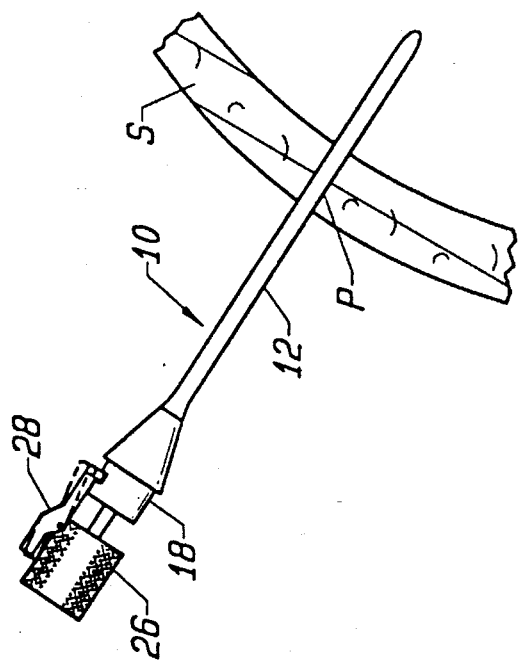
Figure 4:
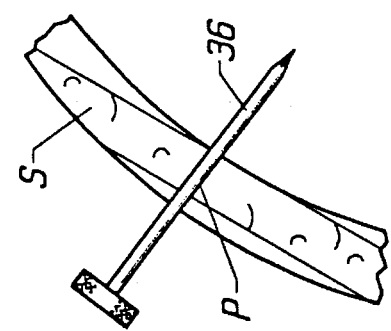
Figure 7:
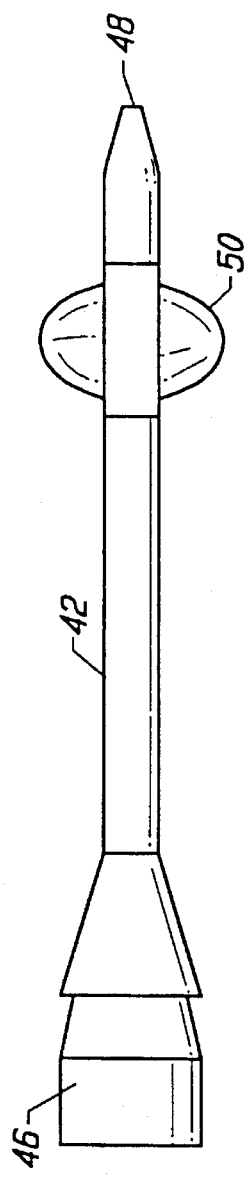
FIGS. 7–10 illustrate the components of a second access tube assembly constructed in accordance with the principles of the present invention.
Figure 8:
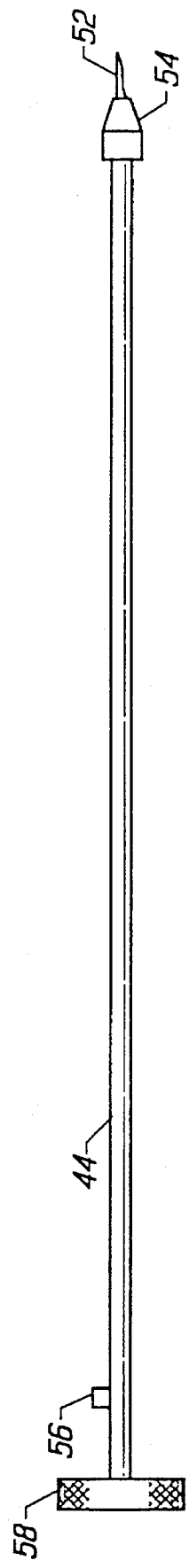

Referring now to FIG. 4–6, use of the access tube assembly 10 for placing the access tube 12 through a patient's skin S is illustrated. With this embodiment, an initial penetration P is formed using a conventional needle or other sharpened instrument 36. The needle 36 is then withdrawn and the access tube assembly 10 having the access tube 12 under axial tension is introduced through the penetration P. It will be appreciated that the reduced diameter of the access tube caused by the axial elongation will facilitate introducing the tube through the penetration. Once the access tube assembly 10 is in place, as illustrated in FIG. 5, the latch 28 may be depressed to release the stylet 14, permitting the access tube 12 to axially shorten and radially expand, as illustrated in FIG. 6. A feeding or drainage tube T can then be connected to the proximal fitting 18 in a conventional manner. For vascular access, the access tube 12 will typically have a hemostatic valve (not shown) on proximal fitting 18.

Figure 9:
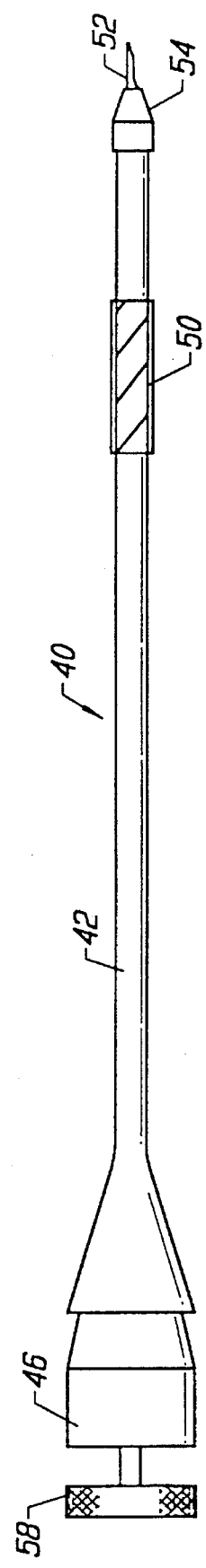

Referring now to FIGS. 7–10, a second access tube assembly 40 is illustrated. The entire access tube assembly 40 is shown in FIG. 9, with the individual access tube 42 and stylet 44 shown in FIGS. 7 and 8, respectively. The access tube 42 is similar in many respects to the access tube 12 described previously. Access tube 42 includes a proximal fitting 46 and has an open distal port 48. An inflatable balloon 50 is located near the distal port 48, and a connector for inflating the balloon 50 will be provided on the proximal fitting 46. To avoid unnecessarily complicating the drawings, the balloon connector fitting is not shown.

The access tube assembly 40 is designed to be self-introducing. In particular, a penetration element 52 is disposed at the distal end of stylet 44. Conveniently, the entire stylet may be formed from hypotube, where the penetration member 52 as defined by a sharpened tip of the hypotube. A collar 54 is disposed on the proximal side of the penetration member 52 and serves to couple the distal end of the access tube 42, as described in more detail hereinafter. A key 56 is formed near the proximal end of the stylet 44 and serves to lock the stylet within a slot (not illustrated) in the proximal fitting 46. A finger grip 58 is disposed at the proximal end of the stylet 44.

Figure 10:
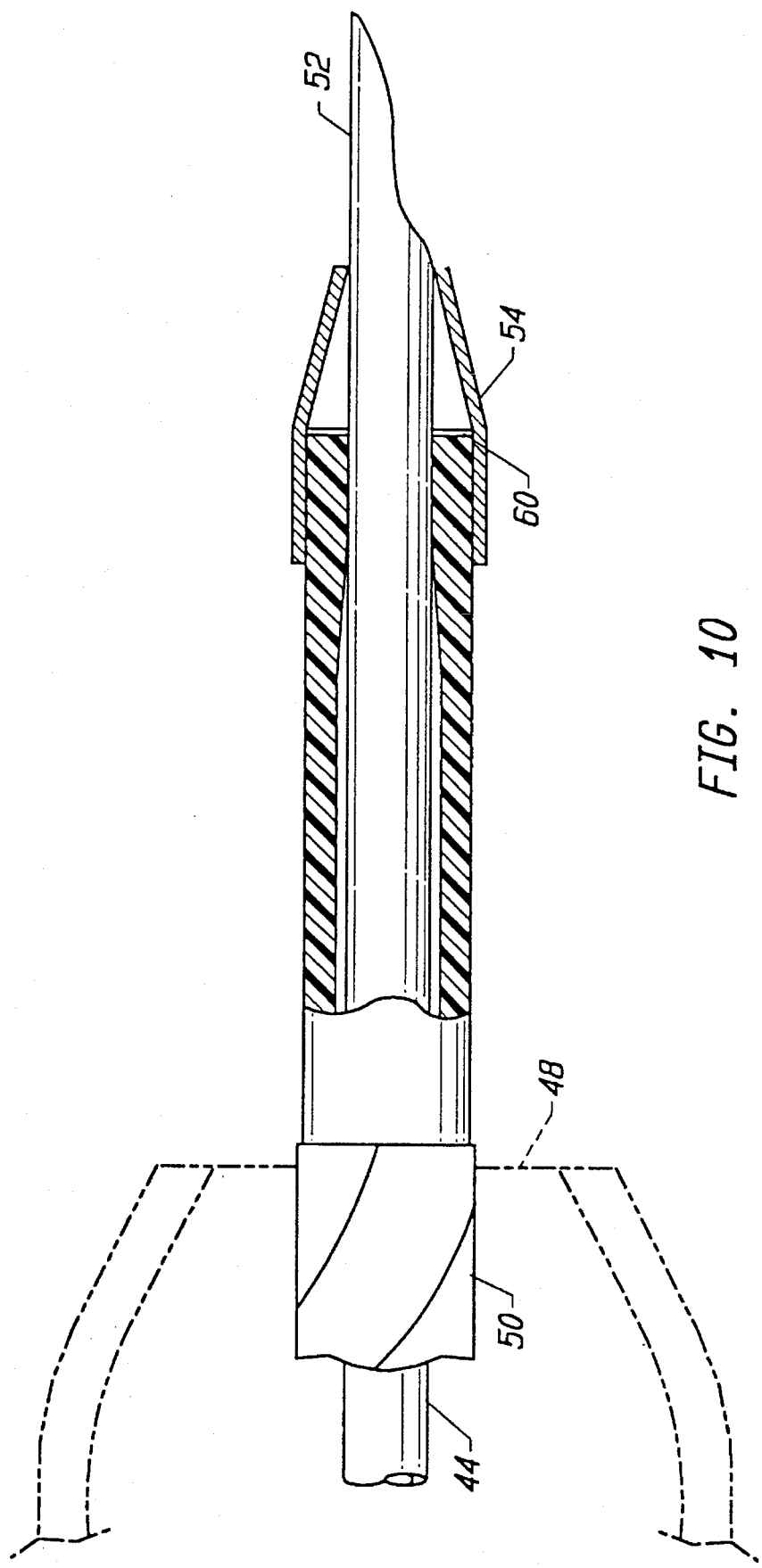

Referring in particular to FIG. 10, the open distal port 48 of the access tube 42 is secured within an annular recess 60 formed between the interior surface of collar 54 and the exterior surface of the hypotube body of stylet 44. The access tube will be held with sufficient strength so that the tube may be axially elongated, as shown in FIG. 9. The configuration of FIG. 9 may be maintained by locking key 56 within the hub to hold the finger grip 58 spaced proximally from the proximal fitting 46, as illustrated. When it is desired to release the distal end of the access tube 42 from the collar 54, the finger grip 58 will be rotated to release the key 56, and the stylet will be further axially advanced to pull the collar off of the access tube. The access tube 42 will then shorten and assume its radially expanded configuration, as shown in broken line in FIG. 10.

Figure 13:
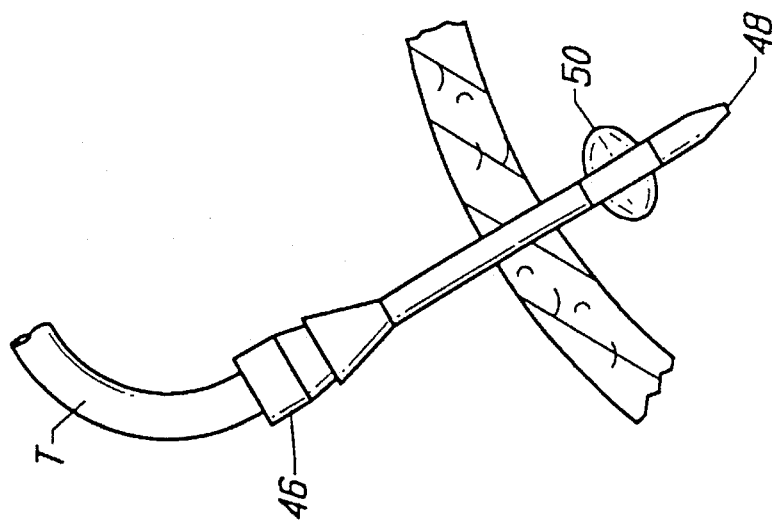
FIGS. 11–13 illustrate use of the access tube assembly of FIGS. 7–10 in placing an access tube through a tissue penetration.
Figure 12:
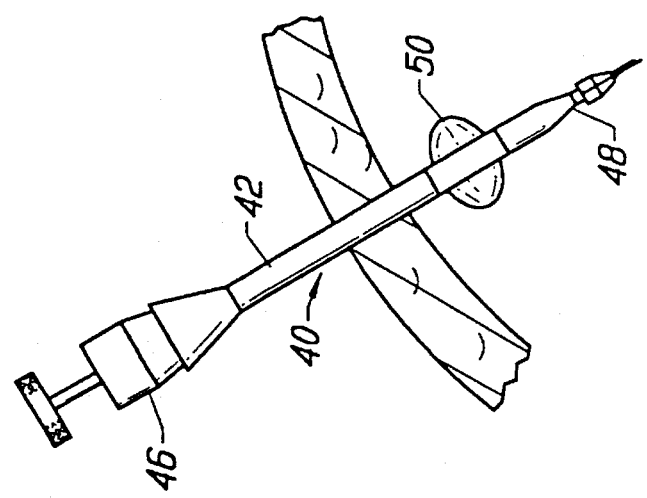
Figure 11:
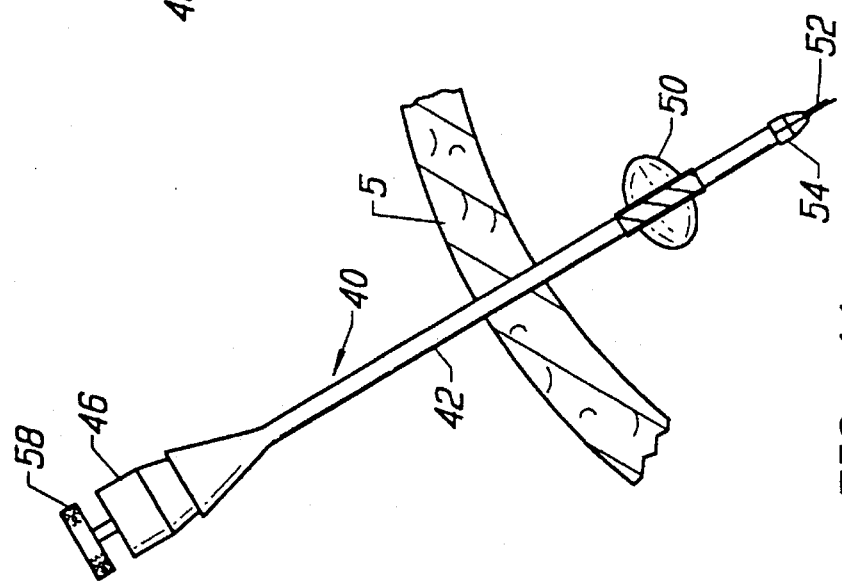

Referring now to FIGS. 11–13, use of the second access tube assembly 40 in percutaneously placing access tube 42 will be discussed. The access tube 40 may be directly introduced through the patient's skin S by piercing the penetrating member 52 at the distal end of the assembly through the skin and any underlying tissue structures to reach the target location. Once introduced, as illustrated in FIG. 11, the balloon 50 may be inflated, and the collar 54 may be axially advanced to release the distal end of the access tube 42, as illustrated in FIG. 12. This is accomplished by depressing the finger grip 58 within the proximal fitting 46, as illustrated. After the distal end has been released, the access tube 42 shortens and assumes its radially expanded configuration. The stylet 44 may then be withdrawn, and a feeding, draining, or other tube T may be connected, as illustrated in FIG. 13. For vascular access, a hemostasis valve (not shown) will be placed on the fitting 46 and no tubing will be connected.

Referring now to FIGS. 14–19, a third access tube assembly including a radially expansible dilation member 110 (FIG. 17) will be described. An access tube 72 has a Malecot structure 74 (illustrated in FIG. 24) at its distal end 76. A proximal housing 78 is similar to the proximal housing 18 illustrated in FIGS. 1–3. A distal portion of the access tube 72 is covered by a removable sheath 80. The sheath 80 will typically have a length from about 10 cm to 20 cm for drainage and feeding tubes or from about 2 cm to 5 cm for vascular access, and will cover approximately half of the access tube 72 in its axially elongated configuration, as illustrated in FIG. 16. The removable sheath 80 will typically be formed from a lubricous plastic, such as a PTFE, FEP, or other plastic. In order to facilitate removal, the sheath will be axially scored or split along a line 82 and will further include a splitable handle 84 at its proximal end. The diameter of the sheath will be approximately equal to that of the access tube 72 in its axially tensioned or stretched condition, i.e., from 2 mm to 8 mm.

A stylet 86 includes an elongate rod 88, a proximal finger grip 90, and a latch member 92. The stylet 86 terminates at its distal end in a blunt tip 94. Stylet 86 is generally the same as stylet 14 illustrated in FIG. 2.

Subassembly 100 comprising the access tube 72 elongated by the stylet 86 is illustrated in FIG. 16. Insertion of the stylet 86 causes the distal end of the assembly to assume a tapered, generally conical configuration as illustrated at 102.

Referring now in particular to FIGS. 17–19, dilation member 110 includes an internal needle assembly 112 in an outer sleeve assembly 114. The needle assembly 112 may be a conventional Veress needle comprising hypotube 116 having a sharpened distal tip 118 and a spring-loaded obturator 120. The obturator 120 retracts while the needle is being penetrated through tissue, but springs back in the distal direction to protect the sharpened tip 118 from unintentionally damaging internal body organs. The Veress needle further includes a proximal connector 122 which permits the introduction of insufflation pressure through an open port 124 on the obturator. The construction of such Veress needles is conventional and well described in the medical and patent literature.

The radially expansible sleeve assembly 114 comprises an inner elastic layer 130, typically formed from latex or silicone rubber, and an outer lubricous covering layer 132, typically formed from PTFE, FEP, or other lubricous material. Veress needle 112 passes through a central lumen of the sleeve assembly 114, and the needle 112 may be withdrawn after the assembly has been percutaneously introduced, as described in more detail hereinafter. The sleeve assembly 114 further includes a proximal handle 134. Preferably, the handle 134 will be splitable and will permit separation and removal of the elastic and lubricous cover layers 130 and 132 after the access tube has been introduced. Conveniently, axial score(s) or split(s) will be formed along line 136 to facilitate such removal.

Figures 20, 21:
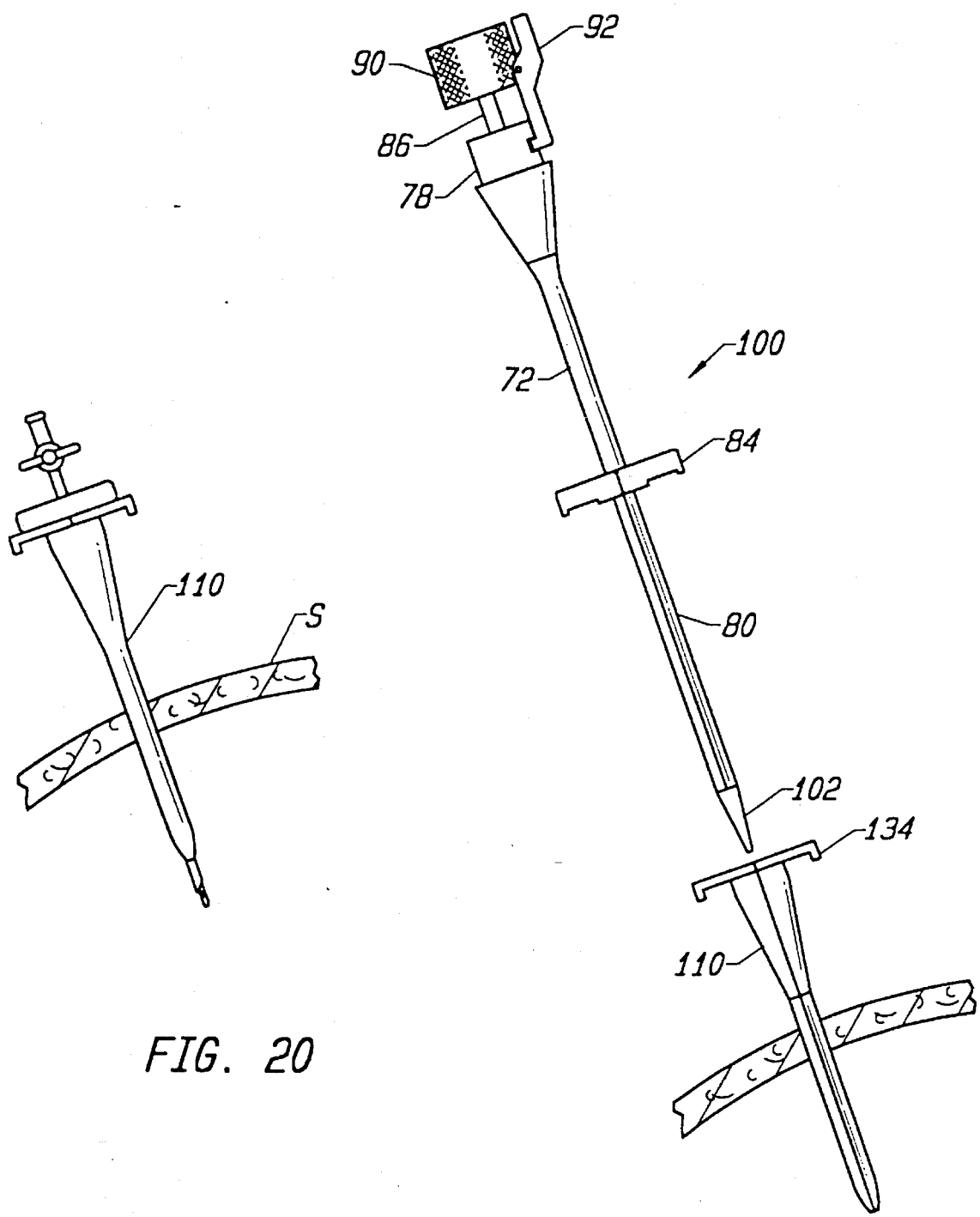

Referring now to FIGS. 20–24, introduction of the access tube 72 using the access tube assembly 70 will be described in detail. Initially, the dilation member 110 is introduced through the patient's skin S, as illustrated in FIG. 20. The dilation member is self-introducing by virtue of the sharpened tip 118 of the Veress needle which is initially located within the dilation member 110. After introduction, the Veress needle 112 is removed, as illustrated in FIG. 21, and the sub-assembly 100 including the access tube 72 and stylet 86 is inserted. The outer diameter the region of the subassembly which is covered by removable sheath 80 has a diameter which is larger than the internal lumen of dilation member 110. Thus, as tapered tip 102 is advanced through the dilation member 110 the diameter of the dilation member will be increased. Once the subassembly 100 is fully introduced, as illustrated in FIG. 22, the sleeve assembly 114 will be expanded along its entire length. The sleeve assembly 114 may then be removed by breaking apart handle 134 and withdrawing the sleeve, as illustrated in FIG. 23. Sheath 80 is then removed by breaking apart handle 134. After the sleeve assembly 114 and sheath 80 have been removed, the stylet 86 may be released by depressing latch member 92, allowing the access tube 72 to fully expand radially as illustrated in FIG. 24.

Although the foregoing invention has been described in some detail by way of illustration and example, for purposes of clarity of understanding, it will be obvious that certain changes and modifications may be practiced within the scope of the appended claims.

What is claimed is:

1. An access tube assembly comprising:
   an elastic access tube having a proximal end, a distal end, and a central lumen extending from the proximal end to the distal end, wherein the tube has an intrinsic length and intrinsic outer diameter when not restrained under axial tension or radial compression;
   a stylet receivable within the central lumen and coupled to the distal end of the elastic access tube; and
   a removable sheath covering at least a distal portion of the elastic tube and having an inner diameter which is less than the intrinsic outer diameter of the elastic tube;
   wherein the elastic access tube is releasably restrained so as to have a reduced outer diameter.

2. An access tube assembly as in claim 1, wherein the elastic access tube has an expandable anchor near its distal end.

3. An access tube assembly as in claim 2, wherein the expandable anchor is a malecot structure which is elongated and collapsed when the stylet engages the distal end of the elastic access tube.

4. An access tube assembly as in claim 2, wherein the expandable anchor is an inflatable balloon.

5. An access tube assembly as in claim 1, wherein the elastic access tube has a closed distal tip which is engaged by the stylet and at least one side port located proximally of the closed distal tip.

6. An access tube assembly as in claim 5, wherein the side port is formed by one or more axial slits which open when the access tube is not under axial tension.

7. An access tube assembly as in claim 1, further comprising a latch mechanism on the stylet for releasably securing the proximal end of the access tube, wherein the latch mechanism is located at a distance from a distal end of the stylet which is at least 20% longer than the intrinsic length of the elastic access tube.

8. An access tube assembly as in claim 7, wherein the elastic access tube has an intrinsic length in the range from 2 cm to 20 cm and an intrinsic outer diameter in the range from 2 mm to 8 mm.

9. An access tube assembly as in claim 8, further comprising a fixture on the proximal end of the elastic access tube, which fixture is secured by the latch mechanism and the latch mechanism is located at a distance from the distal end of the stylet in the range from 3 cm to 40 cm.

10. An access tube assembly as in claim 1, wherein the removable sheath is a polymeric tube having an inside diameter in the range from 2 mm to 8 mm.

11. An access tube assembly as in claim 10, wherein the polymeric tube is axially scored or split on at least one side to facilitate splitting and removing of the sheath.

12. An access tube assembly comprising:
    an elastic access tube having a proximal end, a distal end, and a central lumen extending from the proximal end to the distal end, wherein the tube has an intrinsic length and intrinsic outer diameter when not under axial tension or radial compression, and a reduced outer diameter when under an axial tension; and
    a stylet having a proximal end and a distal end and being receivable within the central lumen of the elastic access tube, wherein the distal end of the stylet is detachably securable to the distal end of the access tube and is capable of applying the axial tension to the elastic tube, and the stylet includes a penetration element at its distal end for facilitating percutaneous introduction.

13. An access tube assembly as in claim 12, wherein the elastic access tube has an expandable anchor near its distal end.

14. An access tube assembly as in claim 13, wherein the expandable anchor is a malecot structure which is elongated and collapsed when the stylet engages the distal end of the elastic access tube.

15. An access tube assembly as in claim 13, wherein the expandable anchor is an inflatable balloon.

16. An access tube assembly as in claim 12, further comprising a latch mechanism on the stylet for releasably securing the proximal end of the access tube, wherein the latch mechanism is located at a distance from a distal end of the stylet which is at least 20% longer than the intrinsic length of the elastic access tube.

17. An access tube assembly as in claim 16, wherein the elastic access tube has an intrinsic length in the range from 2 cm to 20 cm and an intrinsic outer diameter in the range from 2 mm to 8 mm.

18. An access tube assembly as in claim 17, further comprising a fixture on the proximal end of the elastic access tube, which fixture is secured by the latch mechanism and the latch mechanism is located at a distance from the distal end of the stylet in the range from 3 cm to 40 cm.

19. An access tube assembly as in claim 12, wherein the penetration element comprises a sharpened distal tip which extends distally beyond the access tube when the stylet is fully received within the access tube.

20. An access tube assembly as in claim 19, wherein the stylet includes a tapered cylinder at its distal end which tapered cylinder defines an annular recess for receiving the distal end of the access tube.

21. An access tube assembly comprising:
    an elongate dilation member including a radially expandable tubular body having a proximal end, a distal end, an axial lumen, and a penetration member at the distal end;
    an elastic access tube having a proximal end, distal end, and a central lumen extending from the proximal end to the distal end, wherein the tube has an intrinsic length and intrinsic outer diameter when not under axial tension or radial compression; and
    a stylet receivable within the central lumen and engagable against the distal end of the elastic access tube, wherein a tapered distal end is formed on the elastic access tube when under axial tension from the stylet, whereby the tapered distal end facilitates introduction of the access tube and stylet through the axial lumen of the elongate dilation member.

22. An access tube assembly as in claim 21, wherein the elongate dilation member further includes a removable sheath formed over the radially expandable tubular body, wherein the sheath covers the tubular body while the elongate dilation member is percutaneously advanced and can thereafter be removed to permit radial expansion of the tubular body as the tapered end of the elastic access tube is advanced through said tubular body.

23. An access tube assembly as in claim 21, wherein the radially expandable tubular body is an elastomeric tube or a tubular braid.

24. An access tube assembly as in claim 21, wherein the penetration member comprises an elongate penetrating element having a sharpened distal tip, which element is removedly received within the axial lumen of the radially expandable tubular body with the sharpened distal tip extending distally therefrom.

25. An access tube assembly as in claim 21, wherein the elongate dilator member further includes an expandable anchor near its distal end.

26. An access tube assembly as in claim 21, wherein the elastic access tube has an expandable anchor near its distal end.

27. An access tube assembly as in claim 26, wherein the expandable anchor is a malecot structure which is elongated and collapsed when the stylet engages the distal end of the elastic access tube.

28. An access tube assembly as in claim 26, wherein the expandable anchor is an inflatable balloon.

29. An access tube assembly as in claim 21, wherein the elastic access tube has a closed distal tip which is engaged by the stylet and at least one side port located proximally of the closed distal tip.

30. An access tube assembly as in claim 29, wherein the side port is formed by one or more axial slits which open when the access tube is not under axial tension.

31. An access tube assembly as in claim 21, further comprising a latch mechanism on the stylet for releasably securing the proximal end of the access tube, wherein the latch mechanism is located at a distance from the distal end of the stylet which is at least 20% longer than the intrinsic length of the elastic access tube.

32. An access tube assembly as in claim 31, wherein the elastic access tube has an intrinsic length in the range from 2 cm to 20 cm and an intrinsic outer diameter in the range from 2 mm to 8 mm.

33. An access tube assembly as in claim 32, further comprising a fixture on the proximal end of the elastic access tube, which fixture is secured by the latch mechanism and the latch mechanism is located at a distance from the distal end of the stylet in the range from 3 cm to 40 cm.

34. An access tube assembly as in claim 21, wherein the removable sheath is a polymeric tube having an inside diameter in the range from 2 mm to 8 mm.

35. An access tube assembly as in claim 34, wherein the polymeric tube is axially scored or slit on at least one side to facilitate splitting and removing of the sheath.

36. A method for introducing and anchoring an access tube in a tissue penetration, said method comprising:

introducing the access tube through the penetration to a target location while the access tube is under sufficient axial tension so that the outer diameter of the tube is at least 10% less than the intrinsic diameter when the tube is not under axial tension; and releasing the axial tension so that the diameter of the tube expands and seals radially against peripheral tissue along the penetration.

37. A method as in claim 36, wherein the target location is a hollow body organ selected from the group consisting of the stomach, the intestines, the kidney, the gall bladder, chest, lungs, peritoneum, blood vessel, and bladder, or is a cyst.

38. A method as in claim 36, wherein the access tube is introduced in a previously formed tissue penetration.

39. A method as in claim 36, wherein the access tube is introduced simultaneously with forming the tissue penetration.

40. A method as in claim 39, wherein the tissue penetration is formed by advancing a penetrating element secured to a distal end of the axially tensioned access tube through the tissue to the target location.

41. A method as in claim 36, wherein the tissue penetration has an effective diameter which is less than the intrinsic diameter of the access tube and wherein sufficient axial tension is placed on the access tube to reduce the outside diameter to less than said effective diameter.

42. A method as in claim 41, wherein the effective diameter of the tissue penetration is in the range from 1 mm to 6 mm, the intrinsic diameter of the access tube is in the range from 2 mm to 8 mm, and the outer diameter of the access tube when introduced under axial tension is in the range from 2 mm to 8 mm.

43. A method as in claim 36, wherein the access tube is covered with a sheath while being introduced through the penetration, further comprising removing the sheath to permit radial expansion of the access tube.

44. A method as in claim 43, wherein the sheath is axially scored or slit along at least one side to facilitate removal.

45. A method as in claim 36, further comprising dilating the tissue being penetrated.

46. A method as in claim 45, wherein the tissue penetration is dilated prior to introducing the access tube.

47. A method as in claim 46, wherein the tissue penetration is dilated as the access tube is introduced.

48. A method as in claim 36, further comprising expanding an anchor near a distal end of the access tube on a posterior side of the tissue penetration.

49. A method as in claim 48, wherein the anchor is a malecot structure which expands as the axial tension on the access tube is released.

50. A method as in claim 48, wherein the anchor is a balloon which is inflated after the access tube has been introduced.

51. A method as in claim 36, further comprising axially extending the access tube over an internal stylet to provide the sufficient axial tension.

52. A method as in claim 51, further comprising removedly securing a proximal end of the access tube to the stylet to maintain the axial tension while the access tube is being introduced.

53. A method as in claim 52, wherein releasing the axial tension comprises releasing the proximal and of the access tube from the stylet whereby the diameter of the access tube increases.

54. A method for introducing and anchoring an access tube in a tissue penetration, said method comprising:

penetrating an elongate dilation member through tissue to a target location;

introducing the access tube through a lumen of the elongate dilation member while the access tube is under sufficient axial tension so that the outer diameter of the tube is at least 10% less than the intrinsic diameter when the tube is not under stress;

removing the elongate dilation member to leave the access tube in the tissue penetration; and releasing the axial tension so that the diameter of the tube expands so as to dilate and seal radially against peripheral tissue along the penetration.

55. A method as in claim 54, wherein the target location is a hollow body organ selected from the group consisting of the stomach, the intestines, the kidney, the gall bladder, chest, lungs, peritoneum, blood vessel, and bladder, or is a cyst.

56. A method as in claim 54, wherein the access tube is introduced through the dilation member substantially immediately after the tissue penetration has been formed.

57. A method as in claim 54, wherein the outer diameter of the access tube when introduced under tension is larger than the lumen diameter of the elongate dilation member, whereby the diameter of the dilation member is radially expanded as the access tube is advanced from a proximal end of the member through a distal end of the member.

58. A method as in claim 57, wherein the lumen diameter of the dilation member is in the range from 1 mm to 6 mm and the outer diameter of the access tube when introduced under axial tension is in the range from 2 mm to 8 mm, and the intrinsic diameter of the access tube is in the range from 5 mm to 8 mm.

59. A method as in claim 54, wherein the access tube is covered with a sheath while being introduced through the lumen of the dilation member, further comprising removing the sheath to permit redial expansion of the access tube.

60. A method as in claim 59, wherein the sheath is axially scored along at least one side to facilitate removal.

61. A method as in claim 54, further comprising expanding on anchor near a distal end of the access tube on a posterior side of the tissue penetration.

62. A method as in claim 61, wherein the anchor is a malecot structure which expands as the axial tension on the access tube is released.

63. A method as in claim 61 wherein the anchor is a balloon which is inflated after the access tube has been introduced.

64. A method as in claim 54, further comprising axially extending the access tube over an internal stylet to provide the sufficient axial tension.

65. A method as in claim 64, further comprising removably securing a proximal end of the access tube to the stylet to maintain the axial tension while the access tube is being introduced.

66. A method as in claim 65, wherein releasing the axial tension comprises releasing the proximal end of the access tube from the stylet.

67. An access tube assembly comprising:

an elastic access tube having a proximal end, a distal end, and a radially sealed central lumen extending from the proximal end to the distal end, wherein the tube has an intrinsic length and intrinsic outer diameter when not restrained under an axial tension or a radial compression;

a stylet receivable within the central lumen and coupled to the distal end of the elastic access tube; and a removable sheath covering at least a distal portion of the elastic tube and having an inner diameter which is less than the intrinsic outer diameter of the elastic tube;

wherein the elastic access tube is releasably restrained so as to have a reduced outer diameter.

68. An access tube assembly as claimed in claim 67, wherein the elastic access tube is releasably restrained under the radial compression by the removable sheath.

69. An access tube assembly as claimed in claim 67, wherein the elastic access tube is releasably restrained under the axial tension by the stylet.

* * * * *